United States Patent [19]

Guthrie et al.

[11] 4,045,472

[45] Aug. 30, 1977

[54] URETHANE POLYTHIOLS

[75] Inventors: James Leverette Guthrie, Ashton; Clifton Leroy Kehr, Silver Spring, both of Md.

[73] Assignee: W. R. Grace & Co., New York, N.Y.

[21] Appl. No.: 640,499

[22] Filed: Dec. 15, 1975

Related U.S. Application Data

[63] Continuation-in-part of Ser. No. 546,707, Feb. 3, 1975, abandoned.

[51] Int. Cl.$^2$ ........................................ C07C 149/437
[52] U.S. Cl. .................... 260/471 C; 260/77.5 CR; 260/468 E; 260/482 B; 260/482 C; 260/609 R; 260/615 R

[58] Field of Search ............ 260/471 C, 468 E, 482 B, 260/482 C

[56] References Cited

U.S. PATENT DOCUMENTS

| 3,883,598 | 5/1975 | Guthrie et al. | 260/471 C |
|---|---|---|---|
| 3,966,794 | 6/1976 | Larsen | 260/471 C |

*Primary Examiner*—Jane S. Myers
*Attorney, Agent, or Firm*—Elton Fisher

[57] ABSTRACT

The novel urethane polythiols of this invention are prepared by reacting: (a) a mono-, di-, or trihydric polythiol with a polymeric isocyanate; or (b) a di- or trihydric polythiol with a diisocyanate.

6 Claims, No Drawings

URETHANE POLYTHIOLS

CROSS-REFERENCE TO RELATED APPLICATIONS

This is a continuation-in-part of copending application Ser. No. 546,707, filed Feb. 3, 1975, and now abandoned.

BACKGROUND OF THE INVENTION

This invention is in the field of polythiols. More particularly, it is in the field of urethane polythiols which can be made by reacting: (a) a mono-, di-, or trihydric polythiol (including a dithiol) with a polymeric isocyanate which is a mixture of methylene diphenyl diisocyanate (MDI) and higher analogs (or homologs) thereof; or (b) a di- or trihydric polythiol (including a dithiol) with a diisocyanate of the type recited in Embodiment A, infra.

Certain urethane polythiols are taught by U.S. Pat. application Ser. No. 408,338 (which is assigned to W. R. Grace & Co.), filed Oct. 23, 1973, and now abandoned, and by U.S. Pat. No. 3,883,598 (Guthrie et al., 260/609R).

MDI and the higher homologs thereof including admixture of MDI and such homologs are well known to those skilled in the art. Such admixtures (which are known as "polymeric isocyanates" and which are commercially available) are described by W. C. Bedoit, Jr. in an article entitled "Polymeric Isocyanates, What are They?" which appeared on pages 1–4 of "Urethanews, Vol. 1, No. 2, (Jan. 1972), The Martin Sweets Company, Inc., Louisville, Ky, 40201.

Bedoit's article teaches that the term "polymeric isocyanate" is a condensation of the term "polymethylene polyphenylisocanate" and that commercially available polymeric isocyanates are actually mixtures of a number of different polymethylene polyphenylisocyanates. Said article further teaches that methylene diphenyl diisocyanate (MDI), which has a functionality of 2, is the simplest molecule present in a mixture comprising a polymeric isocyanate and that such mixture also contains a trimer having a functionality of 3, a tetramer having a functionality of 4, a pentamer having a functionality of 5, plus higher molecular weight molecules (analogs) having higher functionalities.

MDI generally constitutes about 50% of such polymeric isocyanate.

In general polymeric isocyanates have an average functionality of about 2–6; however, this can be varied by increasing or decreasing the ratio of MDI to the higher (trimer, tetramer, pentamer, etc.) polymers in a mixture comprising a polymeric isocyanate.

SUMMARY OF THE INVENTION

In summary, this invention is directed to a urethane polythiol prepared by admixing and reacting a mono-, di-, or trihydric polythiol (including a dithiol) having the formula

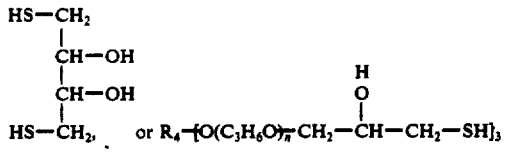

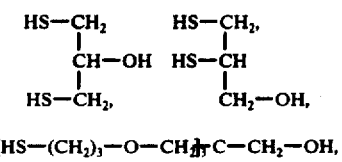

in which $R_4$ is a trivalent saturated hydrocarbon moiety consisting of carbon and hydrogen and having 12–24 carbon atoms and $n$ is 1–2 and an isocyanate consisting essentially of a mixture of methylene diphenyl diisocyanate and higher analogs thereof, the isocyanate and the mono-, di-, or trihydric polythiol being admixed in amounts to provide 1 equivalent of —NCO per 0.5–2 equivalent of —OH.

DESCRIPTION OF PREFERRED EMBODIMENTS

In preferred embodiments of this invention as recited in the above Summary:

The urethane polythiol is prepared by admixing and reacting: (a) a di- or trihydric polythiol having the formula

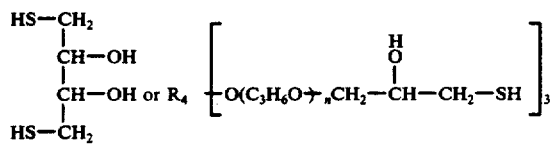

in which $R_4$ is as defined in said Summary; and (b) the mixture of methylene diphenyl diisocyanate and higher analogs thereof described in said Summary, the isocyanate and the di- or trihydric polythiol being admixed in amounts to provide 1 equivalent of —NCO per 0.5–2 equivalent of —OH.

The isocyanate and polythiol are generally admixed in amounts such that the equivalent ratio of —NCO to —OH is 1:0.5–1.2.

In another preferred embodiment ("Embodiment A") this invention is directed to a urethane polyol prepared by admixing and reacting a monohydric polythiol having the formula

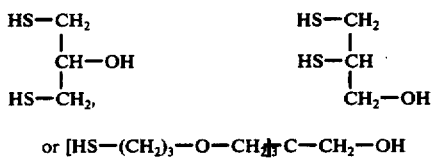

and an isocyanate consisting essentially of a mixture of methylene diphenyl diisocyanate and higher analogs thereof, the isocyanate and the polythiol being admixed in amounts to provide 1 equivalent of —NCO per 0.5–2 equivalents of —OH (or 1 equivalent of —NCO per 0.5–1.2 equivalents of —OH). The resulting urethane polythiol will inherently contain the following compounds:

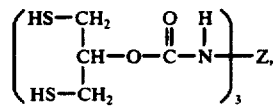

-continued

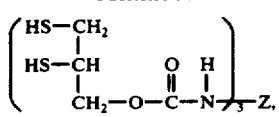

or 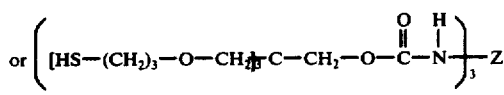

in which Z is

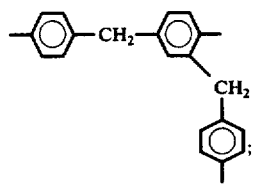

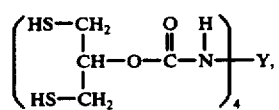

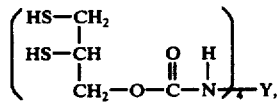

or 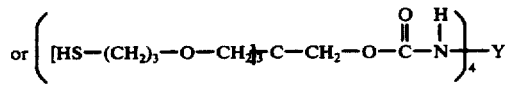

in which Y is

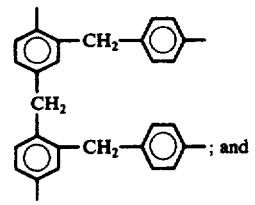

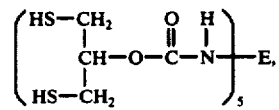

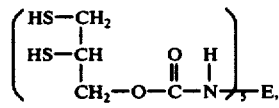

or 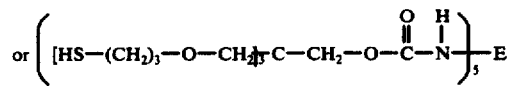

in which E is

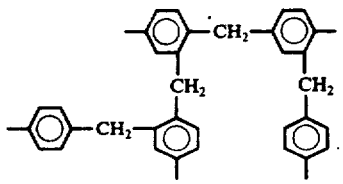

In another preferred embodiment ("Embodiment B") this invention is directed to a urethane polythiol prepared by admixing and reacting: (a) a di- or trihydric polythiol having the formula

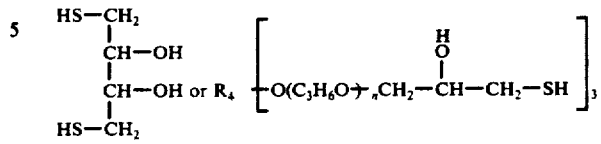

in which $R_4$ is a saturated trivalent hydrocarbon moiety consisting of carbon and hydrogen and having 12–24 carbon atoms and $n$ is 1–2; and (b) a diisocyanate selected from the group consisting of

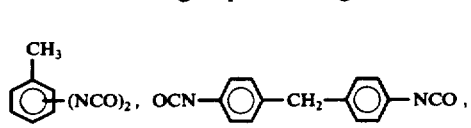

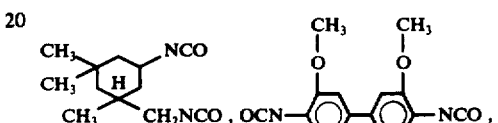

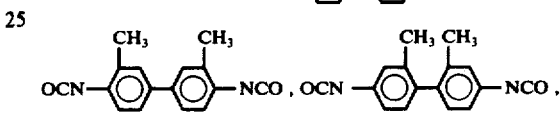

and OCN—$CH_2(CH_2)_4CH_2$—NCO, the diisocyanate and the di- or trihydric polythiol being admixed in amounts to provide 1 equivalent of —NCO per 0.5–2 equivalent of —OH (or 1 equivalent of —NCO per 0.5—1.2 equivalents of —OH).

Detailed Description of the Invention

It is an object of this invention to provide polythiols which can be reacted with polyenes to form polymers. An admixture of such polythiol and such polyene can be polymerized by irradiation with actinic light — preferably after admixing a photocuring rate accelerator such as benzophenone, acetophenone, or the like, with the admixture of polythiol and polyene. An admixture of such polythiol and such polyene can be cured with a peroxide free radical initiator such as methyl ethyl ketone peroxide or the like. Such polymers are useful:

1. For preparing printing plates.
2. For preparing protective coatings on surfaces including wooden and metallic surfaces.
3. As photoresists where etching designs on metallic surfaces.
4. As bonding agents for laminating (bonding) two or more substrates together.

The following are among the many U.S. Pat. Nos. which teach the reaction of polythiols with polyenes to form polymers:

3,535,193 (Prince, 161/88)
3,578,614 (Wszolek, 260/13)
3,615,450 (Werber et al., 95/35.1)
3,660,088 (Lundsager, 96/36)
3,660,217 (Kehr et al., 161/68)
3,661,744 (Kehr et al., 204/159.14)
3,662,022 (Lard, 260/837R)
3,662,023 (Kehr et al., 260/858)
3,676,283 (Kehr et al., 161/88)
3,725,228 (Kehr et al., 204/159.14)

3,725,229 (Kehr et al., 204/159.14)
3,728,240 (Lard, 204/159.16)
3,835,085 (Wrzesinski, 204/159.23).

As used herein, the term "polythiol" means a thiol which contains at least 2 SH groups per molecule (i.e., it has a functionality of at least 2). The term "thiol" is defined by Paterson, J. Am. Chem. Soc., 1933, 55, 3905, 3914, and Chemical Abstracts, 1971, 74, page 24 (Abstract No. 77004q) illustrates the use of the term "polythiol".

As used herein, the term "polyene" means a polyfunctional compound having at least 2 terminal reactive ethylenically unsaturated carbon-to-carbon bonds per molecule (i.e., it has a functionality of at least 2).

As is well known to those skilled in the art, the total functionality of the polythiol plus the polyene with which it reacts to form a polymer must be greater than 4 and neither the polythiol nor the polyene (polyfunctional compound) can have a functionality less than 2.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, will illustrate certain embodiments of our invention.

EXAMPLE 1

Preparation of Triallyl Ether of Pentaerythritol

Into a 5 liter three-necked flask fitted with condenser and addition funnel was placed a solution of 650 g (16.25 equivalents) of sodiium hydroxide in 650 ml of water. To this was added 272 g (two moles) of pentaerythritol. This mixture was stirred by means of a magnetic bar and heated to 70° C. Then 1936 g (1385 ml, 16 moles) of allyl bromide was added over an eight-hour period at such a rate that the temperature stayed between 70° and 80° C. Following this, heating was resumed, keeping the temperature at 80°-82° C for an additional 4 hours. Volatile materials were removed by distillation at atmospheric pressure until the temperature of the condensing vapor reached 98° C.

One liter of water was added to the hot residue (to prevent crystallization of the salts). The product was cooled to room temperature and the layers were separated. The water layer was extracted twice with 300 ml portions of diethyl ether. The combined organic layers were dried over anhydrous magnesium sulfate and then distilled at atmospheric pressure to remove the diethyl ether. The triallyl ether of pentaerythritol product, i.e.,

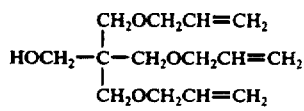

weighed 451 g (88% conversion, one pass yield). The infrared and NMR spectra were those expected for the triallyl ether of pentaerythritol. The triallyl ether of pentaerythritol product had a boiling range of 120°-121° C at 1 mm of mercury absolute pressure, $n_D^{24}$ 1.4625.

EXAMPLE 2

Conversion of Triallyl Ether to Trithiol

Ten drops of tert-butyl hydroperoxide was added to 85.2 g (1 equivalent of unsaturation) of pentaerythritol triallyl ether from Example 1 in a 500 ml flask equipped with a condenser and magnetic stirrer. This mixture was heated to 40° C, and 76 g (1 mole) of thiolacetic acid was added during 1 hour at such a rate that the temperature did not exceed 90° C. After the addition was complete, the product was kept at 80° C for an hour and then allowed to cool to room temperature overnight.

To the product was separation a solution of 100 g (2.5 equivalents) of sodium hydroxide in 200 ml of water. This mixture was heated under reflux for 3 hours and then cooled to room temperature and diluted with 300 ml of ether to facilitate separation of the layers. After separation, the water layer was acidified to pH 2-5 with HCl and then extracted twice with 400 ml portions of ether. Ether was evaporated from the combined organic layers, and the residue was diluted with an equal volume of toluene. The resulting solution was washed with 5% aqueous sodium bicarbonate, then with 5% aqueous hydrochloric acid, and with water. The toluene and other volatile contaminants were removed by distillation at 0.1 mm of mercury absolute pressure until the temperature of the residue reached 225° C. The product (pentaerythritol tris (β-mercaptopropyl) ether, i.e.,

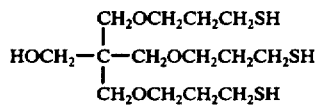

weighed 119 g (100% conversion) and had a mercaptan content of 7.57 milliequivalents per gram. This is 90% of the theoretical amount. This monohydric thrithiol was designated "Polythiol No. 1".

Part of this trithiol (Polythiol No. 1) was distilled at 0.1 mm mercury. The distillate had a boiling range of 243°-245° C.

Procedures for Preparing Urethane Polythiols

Urethane polythiols of the type set forth in the above Summary and Preferred Embodiments can be prepared by the following procedures:

Procedure No. 1

A polythiol having the formula

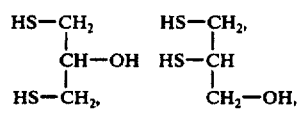

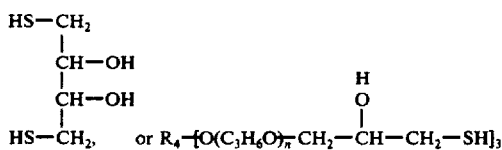

in which $R_4$ is a trivalent saturated hydrocarbon moiety consisting of carbon and hydrogen and having 12-24 carbon atoms and n is 1-2 and a polymeric isocyanate of the type described supra (i.e., a mixture of MDI and higher analogs thereof) can be admixed at 0°-100° C (preferably at 15°-40° C) in amounts to provide an equivalent ratio of —NCO to —OH of 1:0.5-2 (or 1:0.5-1.2 or 1:0.9-1.1). Reaction will generally start substantially as soon as the polythiol and isocyanate are admixed and will generally be completed in about 0.2-24 hours (usually 1-2 hours or less). The major portion of the —NCO groups which react will react with —OH groups of the polythiol and only a minor portion of said —NCO groups will react with —SH groups of the polythiol. Thus, the major product will be a urethane polythiol.

Where the polythiol is

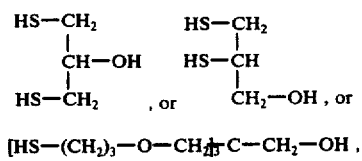

major products will be a mixture of

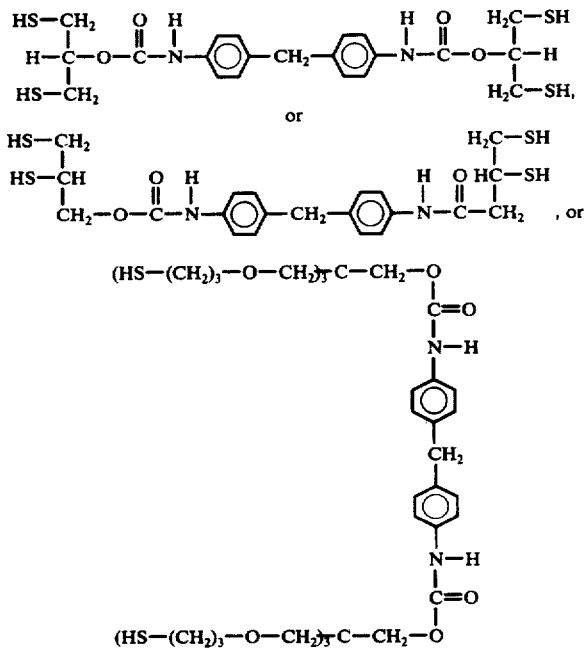

plus corresponding urethane polythiols having the formulas shown in Embodiment A, supra, wherein the polythiol moiety corresponds to the monohydric polythiol reacted.

The reacted mass can be tested for unreacted isocyanate groups (e.g., by infrared sepctroscopy) to determine when the reaction is completed.

Procedure No. 2

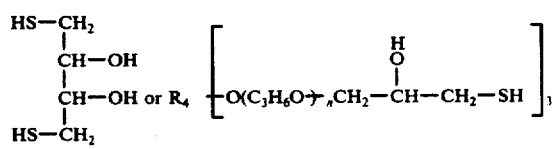

in which R₄ is a trivalent saturated hydrocarbon moiety consisting of carbon and hydrogen and having 12-24 carbon atoms and n is 1-2 and a diisocyanate having the formula

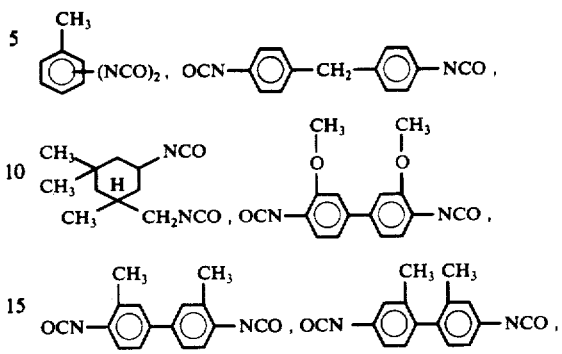

or OCN—CH₂(CH₂)₄CH₂—NCO, are admixed at 0°-100° C (preferably at about 15°-40° C) in amounts to provide an equivalent ratio of —NCO to —OH of 1:0.5-1:2 (preferably 1:0.9-1.1). Reaction generally starts substantially as soon as the polythiol and diisocyanate are admixed and is generally completed in about 1-2 hours.

The major portion of the —NCO groups which react will react with —OH groups of the polythiol and only a minor portion of said —NCO groups will react with —SH groups of the polythiol. Thus the major product will be a urethane polythiol.

The reacted mass can be tested for unreacted isocyanate groups (e.g., by infrared spectroscopy) to determine when the reaction is completed.

As used herein the term "equivalent" as applied to the —OH group means 17 g of said group. Thus one mole of

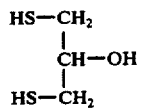

will provide 1 equivalent of —OH and ½ mole of

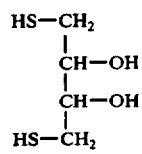

will provide 1 equivalent of —OH.

As used herein the term "equivalent" as applied to the —NCO group means 42 g of said group. Thus 1 mole of a monoisocyanate (such as phenyl isocyanate) will provide 1 equivalent of —NCO and ½ mole of a pure toluene diisocyanate will provide 1 equivalent of —NCO.

As used herein the term "polythiol" includes dithiols.

As used herein the term "mole" has its generally accepted meaning, that is, a mole of a substance contains the same number of molecules of the substance as there are carbon atoms in 12 g of pure ¹²C.

"Functionality" as applied to an isocyanate means the number of —NCO groups per molecule. In mixtures such as polymeric isocyanates, the functionality is the average number of —NCO groups per average molecule.

"Functionality" as applied to a polythiol means the number of —SH groups per molecule.

"Functionality" as applied to a polyene means the number of reactive terminal ethylenically unsaturated groups per molecule.

We claim:

1. A urethane polythiol prepared by admixing and reacting at 0°-100° C: (a) a di- or trihydric polythiol having the formula

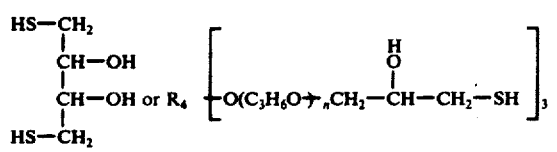

in which $R_4$ is a saturated trivalent hydrocarbon moiety having 12-24 carbon atoms and $n$ is 1-2; and (b) a diisocyanate selected from the group consisting of

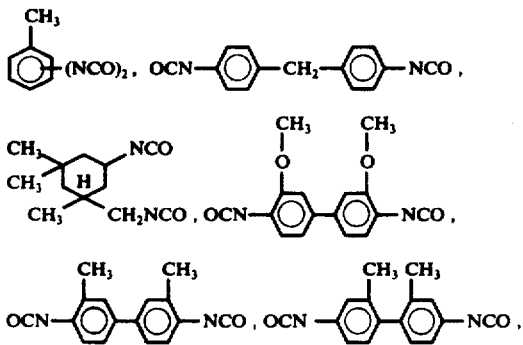

, and OCN—$CH_2(CH_2)_4CH_2$—NCO, the diisocyanate and the di- or trihydric polythiol being admixed in amounts to provide 1 equivalent of —NCO per 0.5-2 equivalent of —OH.

2. The urethane polythiol of claim 1 in which the reaction temperature is 15°-40° C.

3. The urethane polythiol of claim 1 in which the diisocyanate and the di- or trihydric polythiol are admixed in amounts to provide an equivalent ratio of —NCO to —OH of 1:0.5-1.2.

4. The urethane polythiol of claim 1, in which the diisocyanate is

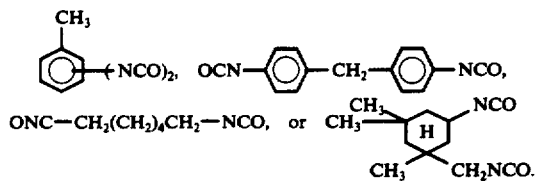

5. A urethane polythiol prepared by admixing and reacting at 0°-100° C: (a) a di- or trihydric polythiol having the formula

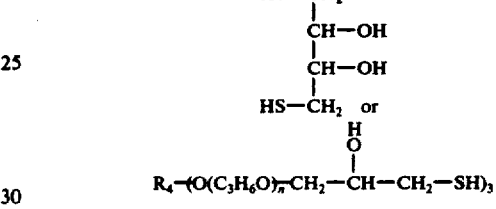

in which $R_4$ is a saturated trivalent hydrocarbon moiety having 12-24 carbon atoms and $n$ is 1-2; and (b) an isocyanate consisting essentially of methylene diphenyl diisocyanate, the isocyanate and the mono-, di-, or trihydric polythiol being admixed in amounts to provide 1 equivalent of —NCO per 0.5-2 equivalent of —OH.

6. The urethane polythiol of claim 5 in which the reaction temperature is 15°-40° C.

* * * * *